United States Patent [19]

Ehrlich

[11] 4,386,608
[45] Jun. 7, 1983

[54] EYE IRRIGATING APPARATUS

[76] Inventor: Kenneth B. Ehrlich, 101 Temple Ave., Manahawkin, N.J. 08050

[21] Appl. No.: 283,555

[22] Filed: Jul. 15, 1981

[51] Int. Cl.³ .............................................. A61M 7/00
[52] U.S. Cl. .................................... 604/298; 604/150; 604/302
[58] Field of Search .............................. 128/249, 248

[56] References Cited

U.S. PATENT DOCUMENTS 2,458,876  1/1949  Rehn ................................... 128/249
4,131,115 12/1978  Peng ................................... 128/249

FOREIGN PATENT DOCUMENTS 1025304  4/1953  France ............................... 128/249
 190022 12/1922  United Kingdom ............... 128/249

Primary Examiner—John D. Yasko
Attorney, Agent, or Firm—Robert A. Green

[57] ABSTRACT

The disclosure is of eye irrigating apparatus comprising a scissors mechanism having two blades, between which a tubular body is positioned, through which an irrigating fluid can flow into the eye from a fluid source.

13 Claims, 7 Drawing Figures

EYE IRRIGATING APPARATUS

BACKGROUND OF THE INVENTION

At the present time, there is no available apparatus which can be used by an individual to spread the eyelids and keep them open for a prolonged period of time, while at the same time providing an unlimited stream of irrigating fluid (not drops), delivered with proper pressure so as to not damage the eye, and directed into the eye to irrigate it of an irritating substance.

The present invention provides such apparatus.

DESCRIPTION OF THE INVENTION

Figure 1:
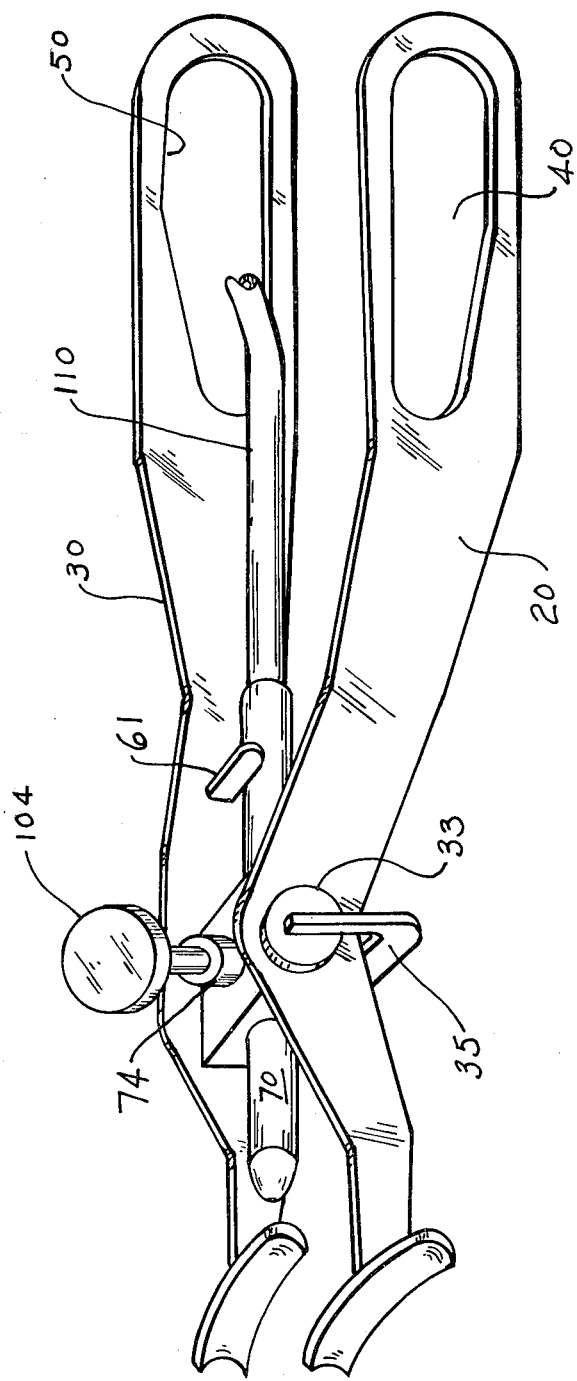
FIG. 1 is a perspective view of the invention.
Figure 2:
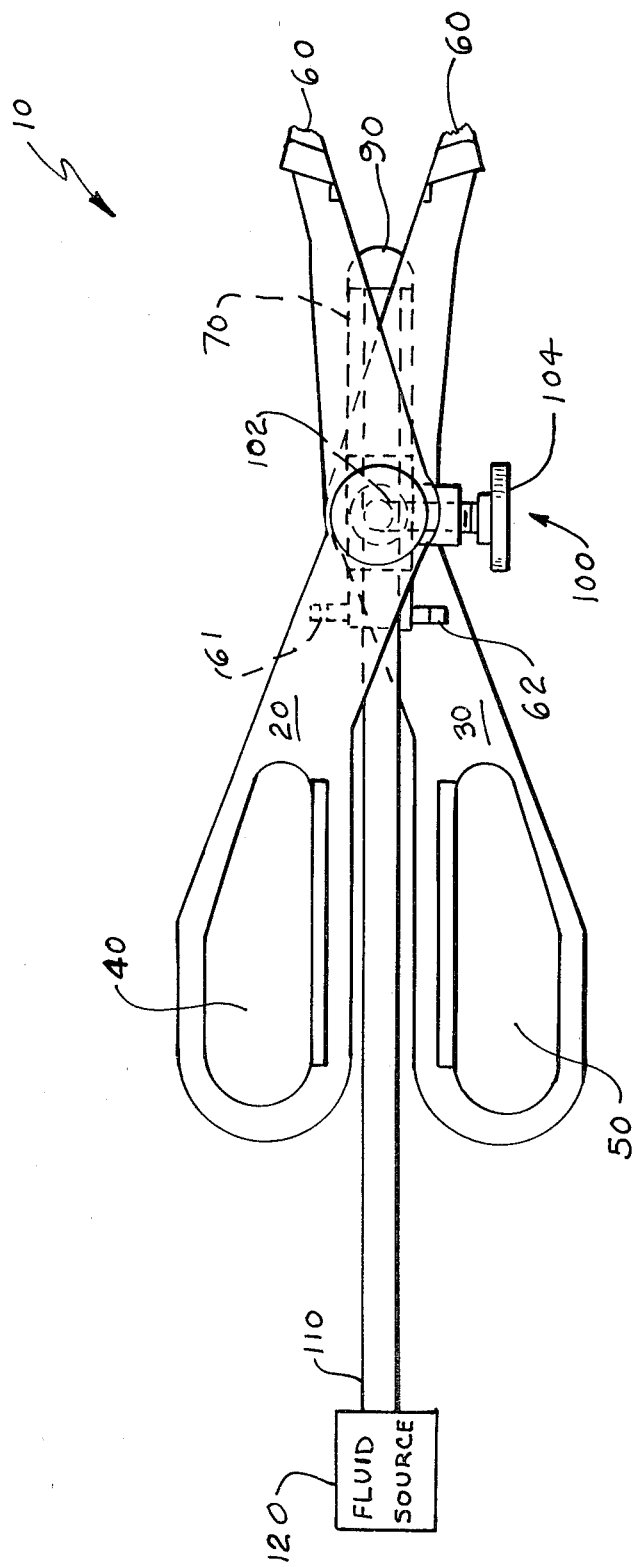
FIG. 2 is a side elevational view of the invention.
Figure 3:
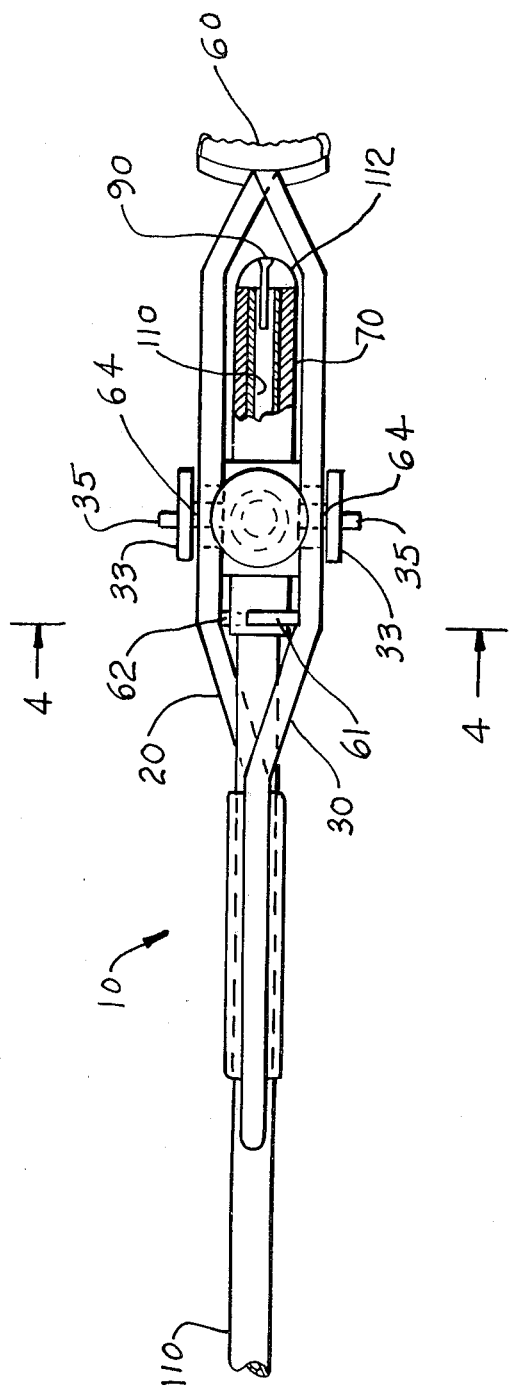
FIG. 3 is a plan view of the apparatus of FIG. 2.

Eye irrigating apparatus embodying the invention 10 comprises a scissors-like apparatus including first and second blades 20 and 30, blade 20 having a finger hole 40, and blade 30 having a finger hole 50 at one end. At the opposite end, each blade has a pad 60 of a soft material such as foam rubber having a surface which is not smooth, but is provided with small bumps or projections which permit frictional engagement of the pads 60 with the eyelids of a person.

The blades 20 and 30 are pivotably coupled together at about their centers about pins or posts 64. In one coupling arrangement, the outer surface of each blade 20, 30 carries a disk 33, and a U-shaped clamp 35 engages the two disks with a tight mechanical fit to hold the parts together. Other coupling arrangements may also be used. The blades 20 and 30 are shaped and arrayed so that the ends of the blades work in opposite directions; that is, when the finger hole portions 40 and 50 are together, the pads 60 are apart, and vice versa. This is done by having the blades not cross each other as in conventional scissors.

Figure 4:
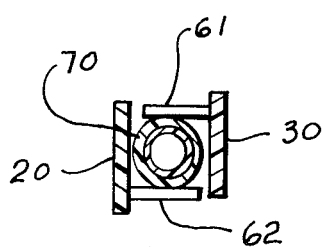
FIG. 4 is a sectional view along the lines 4—4 in FIG. 3.
Figure 5:
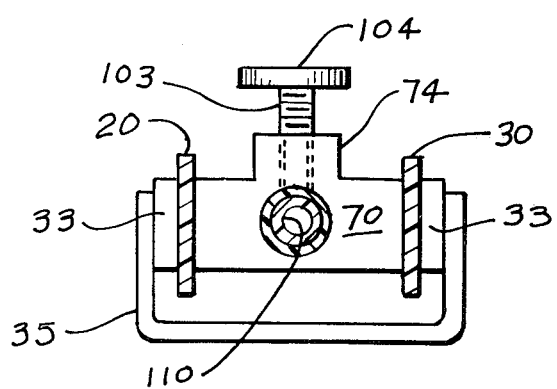
FIG. 5 is a view, partly in section, through the invention near its center.
Figure 6:
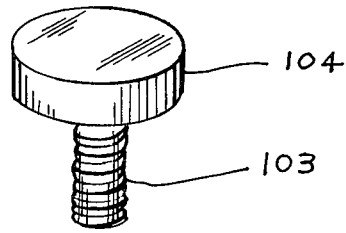
FIG. 6 is a perspective view of a portion of the invention.

Each blade carries a raised stud 61 and 62 on its inner face, just rearward of the pivot points 64. The studs extend toward each other, but they are offset one above the other (FIG. 4) for a purpose to be described.

A tubular plastic valve body 70, through which the irrigating fluid flows, is positioned between the blades 20 and 30 which are suitably shaped for this purpose. The valve body 70 is held in place, for example, by means of the pins or posts 64, about which the blades 20 and 30 are free to pivot or rotate with respect to each other.

A flexible plastic tube 110 is disposed within the valve body, and a separate nozzle or tip 112 is secured to the front end of the flexible tube, and it is suitably secured or cemented to the front end 72 of the valve body 70. The flexible tube 110 has its remote end provided with means for connection to a fluid source 120, for example, a water faucet. The valve body 70 is provided with a threaded hub 74 which is adapted to receive a threaded shaft 103 which can be threaded into and out of the hub 74 by knob 104 to close off or open the flexible tubing 110 within body 70, as required to control the flow of fluid therethrough in operation of the apparatus.

The nozzle 112 has a flared opening 90 at its discharge end which is positioned near the pads 60. The discharge opening 90 flares to a diameter of about 0.060 inch.

In operation of the invention, the device 10 is preferably calibrated by having the tubing 110 connected to source 120, such as a water faucet or the like, to which it might be conveniently, but not necessarily, always connected and ready for use. The source 120 is turned on to maximum flow, and the valve knob 104 is manipulated to set the shaft 103 in the valve body 70 at the proper depth and contact with tubing 110 to provide the desired flow of water out of the tube 110. Uncontrolled high pressure flow might damage the eye, and it is undesirable to take time to set the flow at the moment when the device is needed for use.

Now, when it is desired to irrigate an eye in which an irritant has entered and whose lids are tightly closed because of the presence of the irritant, with water flowing out of the opening 90 in the tube 70, and with finger hole portions open and pads closed, the operator places the closed pads 60 on the two eyelids, and, by closing the finger hole portions 40 and 50, the pads are moved apart, the eye is exposed and fluid enters the eye at a favorable rate of flow. Additional ease of operation can be achieved in some cases by using one hand to assist in the elevation of the upper eyelid. Fingertips exert upward pressure in the region of the eyebrow/lid to assist the device in initially opening the eye. The fluid flow is continued for as long as required to cleanse and irrigate the eye of the irritating substance present.

The present medical consensus for the best immediate treatment of a caustic substance in the eye is by thoroughly irrigating the open eye continuously, but for short breaks, for at least 15 minutes.

It is noted that, when the blades are closed (FIGS. 1 and 4), the raised studs or posts 61 and 62 engage the valve body 70 and properly center it so that the desired directional flow of fluid into the eye is achieved.

Figure 7:
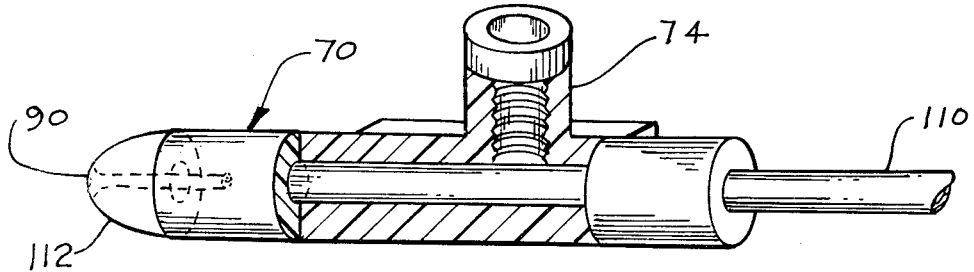
FIG. 7 is a side view of a modification of a portion of the invention.
Figure 7:
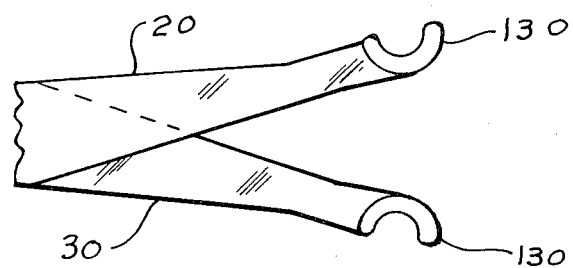

In a modification of the invention for professional use, the leading ends of the blades 20 and 30 which engage the eyelids are provided with occular speculum-type members 130 (FIG. 7) which engage and hold the eyelids open in well known fashion. Other end structures might also be used.

Some of the advantages of the invention include: The provision of an unlimited source of universally available irrigation fluid delivered at a safe (preadjusted) rate of pressure which permits immediate, maximum and most effective irrigation of the eye; Elimination of the need for manual manipulation of the eyelids, therefore permitting more complete, prolonged irrigation for optimum treatment; Formal training is not required and the apparatus can be operated easily by the patient or any other person; A local anesthetic is not required.

What is claimed is:

1. Eye irrigation apparatus comprising
    a scissors-like mechanism comprising two blades which are pivotably connected at about their centers,
    first means comprising a tubular valve body disposed between said blades and adapted to receive fluid from a source and positioned to provide a stream of fluid into the eye when the apparatus is disposed in operative relation with the eye, an adjustable valve in said tubular body of said first means for controlling the flow of fluid therethrough, said first means including a body portion disposed between said blades and engaged by said blades whereby said first means is supported between said blades, and auxiliary support means on said blades for engaging said first means and maintaining said first means positioned properly so that fluid is directed at the eye.

2. Eye irrigation apparatus comprising a scissors-like mechanism comprising two blades, each having a finger hole at one end and eyelid engaging means at the other end, said blades being pivotably connected at about their centers, first means comprising a tubular valve body disposed between said blades and adapted to receive an eye-washing fluid from a source and positioned so that fluid flowing out of said means flows into and irrigates the eye when the apparatus is disposed in operative relation with the eye, said first means including a body portion disposed between said blades and engaged by said blades whereby said first means is supported between said blades, and auxiliary support means on said blades for engaging said first means and maintaining said first means positioned properly so that fluid is directed at the eye.

3. The apparatus defined in claim 2 wherein said eyelid engaging means comprises soft friction pads which can engage and move the eyelids as they move apart.

4. The apparatus defined in claim 2 wherein said eyelid engaging means comprises optical speculum-type members.

5. The apparatus defined in claim 2 and including a flexible tube within said valve body, said flexible tube receiving the fluid used to irrigate the eye.

6. The apparatus defined in claim 5 and including means in said valve body for controlling the flow of fluid therethrough and into the eye whereby a safe pressure of fluid strikes the eye.

7. The apparatus defined in claim 2 and including a raised stud on each blade and positioned to hold said valve body between them when the apparatus is in operation whereby the valve body is held and aimed properly so that fluid is directed at the eye as desired.

8. The apparatus defined in claim 7 wherein said studs are on the facing inner surfaces of said blades rearwardly of the centers of said blades and near the rear end of said valve body.

9. Eye irrigation apparatus comprising a scissors-like mechanism comprising two blades, each having a finger hole at one end and eyelid engaging means at the other end, said blades being pivotably connected at about their centers and arrayed so that, when the finger hole ends are close together, the other ends are open and spread apart, and vice versa, means for providing a stream of an eye-washing fluid disposed between said blades and positioned so that fluid flowing out of said means irrigates the eye when the apparatus is disposed in operative relation with the eye, said means comprising a tubular valve body disposed between said blades and adapted to receive fluid from a source and to direct the fluid into the eye, and a raised stud on each blade and positioned to hold said valve body between them when the apparatus is in operation whereby the valve body is held and aimed properly so that fluid is directed at the eye as desired.

10. The apparatus defined in claim 1 and including a flexible tube within said tubular body, said flexible tube receiving the fluid used to irrigate the eye.

11. The apparatus defined in claim 1 wherein said first means contains a flexible tube which extends out of said first means and is connectable to a source of fluid, and said body portion of said first means includes said adjustable valve which is adapted to engage said flexible tube to control the flow of fluid therethrough.

12. The apparatus defined in claim 1 wherein said body portion of said first means is pivotably coupled to said blades whereby said blades can pivot with respect to said first means.

13. Eye irrigation apparatus comprising a scissors-like mechanism comprising two blades which are pivotably connected at about their centers, and a tubular member between said blades for providing a stream of an eye-washing fluid disposed between said blades and positioned so that fluid flowing out of said means irrigates the eye when the apparatus is disposed in operative relation with the eye, said tubular member including a body portion engaged by said blades whereby said tubular member is supported between said blades, said body portion including a valve adjustably mounted for entering said body portion and controlling the pressure of the flow of fluid therethrough.

* * * * *